United States Patent

Wolcott

[11] Patent Number: 5,846,182
[45] Date of Patent: Dec. 8, 1998

[54] ESOPHAGEAL OVERTUBE FOR SMOKE EVACUATION

[75] Inventor: Kenneth E. Wolcott, Freeport, N.Y.

[73] Assignee: Olympus America, Inc., Melville, N.Y.

[21] Appl. No.: 929,410

[22] Filed: Sep. 15, 1997

[51] Int. Cl.⁶ .................................................. A61B 1/04
[52] U.S. Cl. ..................... 600/114; 600/120; 128/207.14
[58] Field of Search .................................. 600/114, 120, 600/121, 125; 128/200.26, 207.14, 207.15

[56] References Cited

U.S. PATENT DOCUMENTS

| | | | |
|---|---|---|---|
| 3,913,565 | 10/1975 | Kawahara | 600/114 X |
| 4,332,242 | 6/1982 | Chikama | 600/114 |
| 4,735,603 | 4/1988 | Goodson et al. | |
| 4,825,861 | 5/1989 | Koss | 128/200.26 X |
| 5,105,800 | 4/1992 | Takahashi et al. | 600/121 |
| 5,199,944 | 4/1993 | Cosmescu | |
| 5,308,317 | 5/1994 | Ferguson et al. | |
| 5,337,733 | 8/1994 | Bauerfeind et al. | 600/114 X |
| 5,368,560 | 11/1994 | Rambo et al. | |
| 5,390,661 | 2/1995 | Griffith et al. | 600/114 |
| 5,431,650 | 7/1995 | Cosmescu | |
| 5,509,892 | 4/1996 | Bonnet | 600/157 X |
| 5,620,408 | 4/1997 | Vennes et al. | 600/120 X |
| B2 4,368,560 | 7/1995 | Wetzel et al. | |

OTHER PUBLICATIONS

C.P. Orsay (1984) "3. Upper Gastrointestinal Endoscopy" R.K. Pearl, *Gastrointestinal Endoscopy for Surgeons* (Boston, MA, and Toronto, Canada: Little, Brown and Company).

"Tube Allure PPC coextrusion" (item) Putnam Plastics Corporation, Dayville, Connecticut.

"Custom thermoplastic extrusion and device fabrication" (brochure) Adam Spence Corporation, Wall, New Jersey, and County Roscommon, Ireland.

J.G. DesCoteaux et al. (1996) "Preliminary study of electocautery smoke particles produced in vitro and during laparoscopic procedures" *Surg. Endosc.* 10(2): 152–158.

K. Hayashi et al. (1996) "Laparoscopic closure for perforation of the sigmoid colon by endoscopic linear stapler" *Surg. Laparosc. Endosc.* 6(5): 411–413.

E. Firoozmand et al. (1996) "Ventricular laceration and cardiac tamponade during laparoscopic Nissen fundoplication" *Surg. Laparosc. Endosc.* 6(5): 394–397.

*Primary Examiner*—Beverly M. Flanagan
*Attorney, Agent, or Firm*—Scully, Scott, Murphy & Presser

[57] ABSTRACT

An esophageal overtube for use with an endoscope in which the overtube has a conduit for evacuation of laser smoke and burnt tissue which is created during esophageal tumor ablation with laser therapy. A vacuum port on the esophageal overtube facilitates connection to a vacuum source which evacuates the laser smoke and burnt tissue to a site remote from the operating environment. An embodiment of the esophageal overtube has a bite block which can be either reusable or detachable from the overtube in a disposable version. Another embodiment of the esophageal overtube has a seal which seals the esophagus from the operating environment. Also disclosed are methods for using the various esophageal overtubes.

19 Claims, 9 Drawing Sheets

ESOPHAGEAL OVERTUBE FOR SMOKE EVACUATION

BACKGROUND OF THE INVENTION

1. Field of the Invention

The field of art to which this invention relates is esophageal overtubes, in particular, esophageal overtubes used in endoscopic procedures in which laser ablation of a tumor is being performed.

2. Description of the Related Art

It is common practice to perform both diagnostic and therapeutic esophageal endoscopy on human medical patients to discover and rectify abnormalities that may occur in the esophagus. For example, endoscopy is frequently used in patients suspected of having reflux esophagitis, benign strictures, esophageal rings, esophageal ulcers, malignant tumors and cancers. These abnormalities may be treated by various techniques, including laser therapy. Laser therapy is especially beneficial in tumor removal and for treatment of esophageal cancers.

Laser therapy for palliative treatment of esophageal tumors is a fairly common procedure. Typically a one or two channeled endoscope is passed into the esophagus, a laser probe is passed down through one of the channels. The laser probe is directed at the tumor and fired, destroying the cancerous tissue. The goal of this procedure is not to completely eliminate the tumor, but to reduce the tumor to a size that makes passage of food and liquids possible, improving the patient's quality of life for their last remaining months.

This procedure, like other endoscopic procedures in the upper gastrointestinal tract, is sometimes performed using an overtube. An overtube is a conduit which is placed in a patient's esophagus by way of the oral cavity. Therefore, the overtube is placed down the esophagus once at the beginning of the procedure, reducing patient discomfort resulting from repeated passes of the endoscope. The overtube also reduces the doctor inconvenience associated with having to make repeated passes of the endoscope during therapy. It being much easier to withdraw and pass the endoscope through the overtube, then to pass it through the oral cavity and esophagus.

Bite blocks are also typically used when performing palliative treatment of esophageal tumors. During the procedure, the bite block is inserted in the patient's mouth for the patient to bite down upon. The bite block has a central cylindrical hole to accommodate the overtube, which is passed through the bite block. The bite block can also be an integral part of the overtube. The main purpose of the bite block is to protect the endoscope from being damaged by the patient's teeth. However, biting down on the bite block also provides the patient with some therapeutic comfort.

Along with the many benefits of laser therapy, there are also certain disadvantages associated with the use of lasers. One such disadvantage is the production of laser smoke and burnt tissue. The laser smoke migrates towards other parts of the body, including the oral cavity, nasal passage, and lungs and is potentially injurious to these tissues. In addition, laser smoke and burnt tissue often collect on the endoscope's lens, obscuring the endoscopist's view through the endoscope. To clean the smoke and tissue from the distal end of the endoscope the endoscopist is forced to repeatedly remove the endoscope in order to clean the lens.

Perhaps the largest disadvantage associated with laser surgery, the harmful effects of which are just being realized, is exposure to the laser smoke by operating room personnel. This is especially true when the smoke results from laser therapy of cancerous tissue, exposing the operating room personnel to cancerous aerosols contained in the laser smoke. This is a real concern, which has recently gotten the attention of the gastrointestinal medical community. Endoscopists are concerned about the possible side effects caused by the exposure to the harmful laser smoke. In fact, a recent study published in *Surgical Endoscopy* in February 1996, at pages 152–158, shows that cancerous cells do exist in laser smoke. However, the potential adverse effects caused by exposure to the smoke was not determined.

An typical endoscope of the prior art used for treatment of both diagnostic and therapeutic esophageal endoscopy is illustrated in FIGS. 1 and 2 and referred to generally by reference numeral 10. The endoscope 10 has a control section 12, an insertion tube 14, and a light guide connector 16. A universal cord 16a containing fiber optics connects the light guide connector 16 to the control head 12. The insertion tube further has a bending section 18 and distal end 20. The bending section is controlled by up/down and right/left angulation knobs 22,24 located on the control head 12.

Referring now to FIG. 2, the distal end 20 has a light guide 20a in which light from a light source travels from the light guide connector 16, through fiber optics contained in the universal cord 16a and insertion tube 14, terminating at the distal end 20. The light from the light guide 20a illuminates the area in front of the distal end 20. The distal end also typically has an objective lens 20b, which could include a CCD camera relaying images to a monitor, or an image bundle of optic fibers which relays the images to an eyepiece (not shown) located on the control head 12. An air/water nozzle 20c directs air or water across the lens for cleaning off debris. The endoscope 10 typically has at least one working channel (not shown) running inside the insertion tube 14. The working channel has an inlet 21 near the control head 12, and an outlet 20d which exits at the distal end 20. Accessories, such as a biopsy forceps or laser probe, are passed from the inlet 21, through the working channel in the insertion tube 14, exiting the distal end 20 at the outlet 20d.

Currently, there are two methods of isolating operating room personnel from the laser smoke produced during the treatment of esophageal tumors: (1) through the endoscope's working channel; or (2) by using a large overhead fume hood. Both of these methods have disadvantages associated with their use.

When using a working channel to evacuate the laser smoke, suction is applied to the working channel inlet 21. A vacuum source which provides the suction is usually available in an operating room or endoscopy suite. However, the laser probe also requires a working channel. Therefore, an endoscope with a minimum of two working channels is required to effectively perform endoscopic laser therapy with smoke evacuation through a working channel. Endoscopes with two working channels need to be larger in cross-sectional diameter to accommodate the additional working channel. The larger cross-sectional area adds to the patients discomfort because a larger endoscope must be used to accommodate the second channel.

In addition, typical working channel cross-sections are very small (typically, 2–3.2 mm in diameter), consequently, air flow through the working channel is limited. Therefore, smoke evacuation through a working channel is not very efficient. A further disadvantage of using a two-channeled endoscope is the cost. Endoscopes with two working channels are not very common, and are therefore expensive.

Lastly, two-channeled endoscopes are bulky and cumbersome to use, requiring dexterity on the part of the doctor to manipulate them.

Using a fume hood to evacuate the laser smoke in an operating room or endoscopy suite also has its disadvantages. The laser smoke is not being evacuated at the site where it is being produced. Therefore, the smoke can adhere to the lens and light guide, obscuring the endoscopist's view. Furthermore, the laser smoke is allowed to drift into the operating room where it is exposed to operating room personnel before being evacuated. Lastly, overhead smoke evacuation hoods are expensive and rarely used in practice.

Accordingly, there is a need in the art for an improved apparatus and method for evacuating laser smoke during endoscopic treatment of esophageal cancer which is safe, inexpensive, efficient, and less traumatizing to the patient.

SUMMARY OF THE INVENTION

Therefore, it is an object of the present invention to provide an esophageal overtube for eliminating the exposure of operating room personnel to cancerous aerosols contained in laser smoke.

It is a further object of the present invention to provide an esophageal overtube which keeps the lens and light guide of an endoscope cleaner, for a longer period of time.

It is yet another object of the present invention to provide an esophageal overtube which reduces doctor inconvenience in repeatedly removing an endoscope for cleaning.

It is yet another object of the present invention to provide an esophageal overtube which reduces the amount of patient discomfort and trauma.

It is yet another object of the present invention to provide an esophageal overtube which eliminates the need for a two-channeled endoscope when performing esophageal laser therapy.

It is yet another object of the present invention to provide an esophageal overtube which eliminates the need for overhead fume hood when performing esophageal laser therapy.

It is yet another object of the present invention to provide an esophageal overtube which reduces the costs associated with endoscopic esophageal laser therapy.

It is yet another object of the present invention to provide an esophageal overtube which increases the efficiency by which laser smoke is evacuated during endoscopic esophageal laser therapy.

It is still yet another object of the present invention to provide an esophageal overtube which reduces the amount of dexterity needed by doctors when performing esophageal laser therapy with a two channel endoscope.

Accordingly, an esophageal overtube is disclosed. The overtube has a tube member having a distal end and a proximal end. The tube member further comprises an outer wall and an inner wall, each wall having an outside and an inside surface. A conduit is defined by the volume between the outside surface of the inner wall and the inside surface of the outer wall. The conduit extends from the distal end to the proximal end of the tube member. The tube member further has a lumen defined by the inside surface of the inner wall. A block is disposed on the proximal end of the tube member. The block has a conduit in direct communication with the conduit of the tube member. The block also has an aperture in direct communication with the lumen of the tube member for passage of an endoscope therethrough. A vacuum port is disposed on the block. The vacuum port has a conduit in direct communication with the conduits of the block and tube member. The vacuum port further having an outlet end for connection to a vacuum source. Smoke is evacuated from the distal end of the tube member through the conduits of the block, tube member, and vacuum port by the vacuum source.

In a version of the above embodiment, the walls of the tube member are circular in cross-section.

In yet another version, in addition to the walls of the tube member being circular in cross-section, they are non-concentric. This arrangement results in the walls intersecting at a point which forms a web connecting the inner wall to the outer wall.

In yet another version, the present invention further comprises at least one web connecting the inner and outer walls of the tube member. The volume between the outside surface of the inner wall, the inside surface of the outer wall and adjacent webs each define a conduit. The number of conduits being equal to the number of webs. A mixing chamber is disposed in the block which has surfaces defining a volume common to all of the conduits wherein the conduit of the block is in direct communication with the mixing chamber. The preferred number of webs being two, defining two conduits of substantially equal volume. However, it is understood that any number of webs can be employed.

In yet another version of the present invention, the block has portions defining a bite block for a patient to bite upon when the esophageal overtube is in place in the patient's esophagus. In a preferred embodiment, the bite block and block define two separate pieces, the bite block portion being disposable. A means to secure the bite block to the block and release the bite block from the block is provided by a projection disposed on the bite block and an opposing indent on the block. The projection and indent interfere with each other to provide a securing means yet easily pull apart to provide a releasing means. A means to locate the bite block onto the block is provided by at least one pin disposed on the block, opposed by bores of substantially the same size and shape as the pins, for acceptance of the pins.

In yet another version of the present invention, the vacuum port further comprises a barbed fitting, luer fitting, or stopcock fitting disposed on the outlet end for facilitating connection to a vacuum source.

In yet still another version of the present invention a sealing means is disposed in the aperture of the block for isolating the lumen of the tube member from the operating environment. A preferred sealing means is provided by an elastomer membrane having an aperture of smaller cross-sectional shape then the cross-sectional shape of the endoscope to be inserted therein. Insertion of the endoscope through the aperture stretches the membrane to conform to the cross-sectional shape of the endoscope thereby isolating the lumen from the operating environment. A securing means is also provided to fix the membrane to the block.

Another aspect of the present invention are methods of using the various embodiments of the present invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENTS

Figure 3:
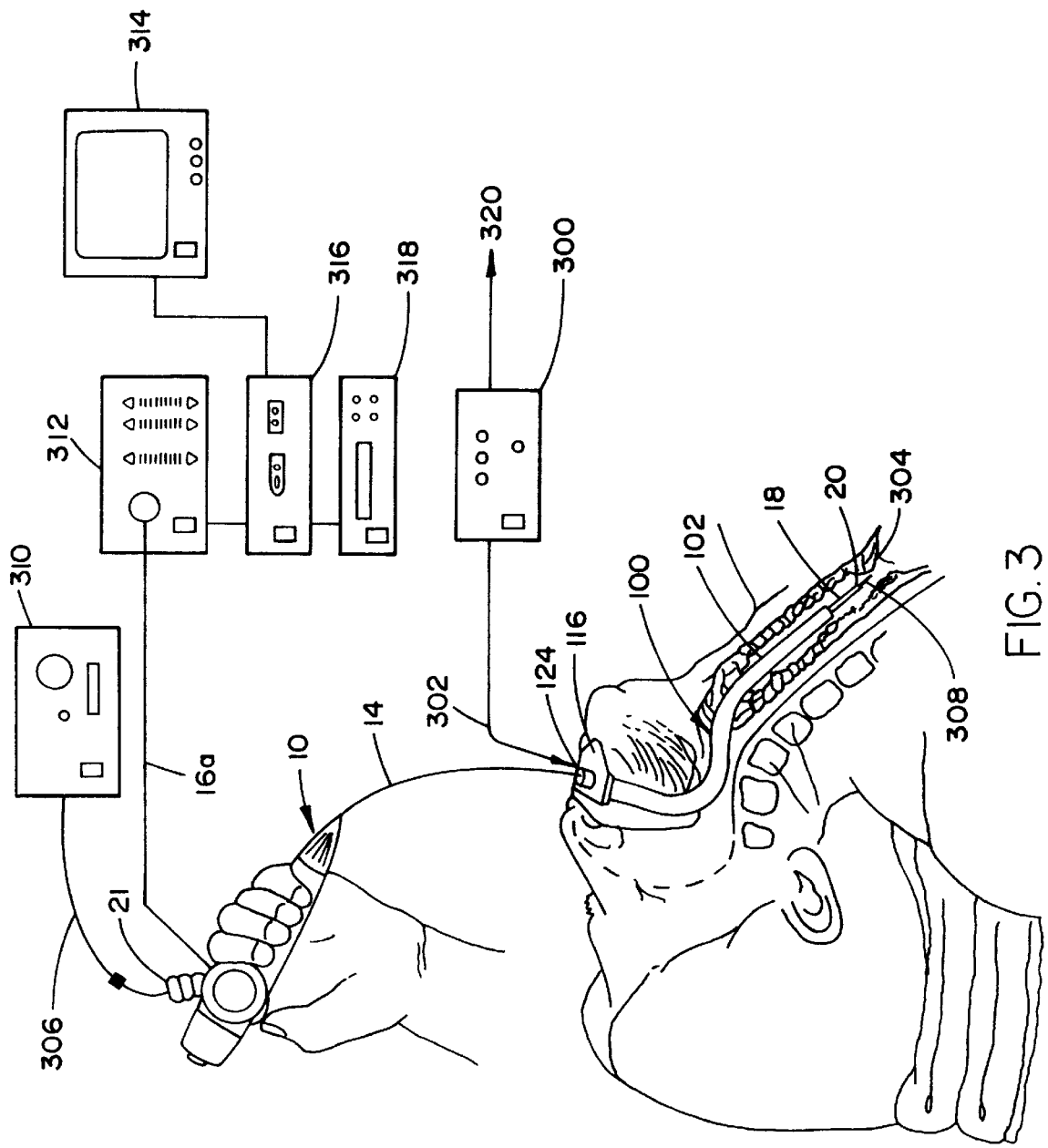
FIG. 3 illustrates the present invention in place in a patient's esophagus during an endoscopic procedure.
Figure 4:
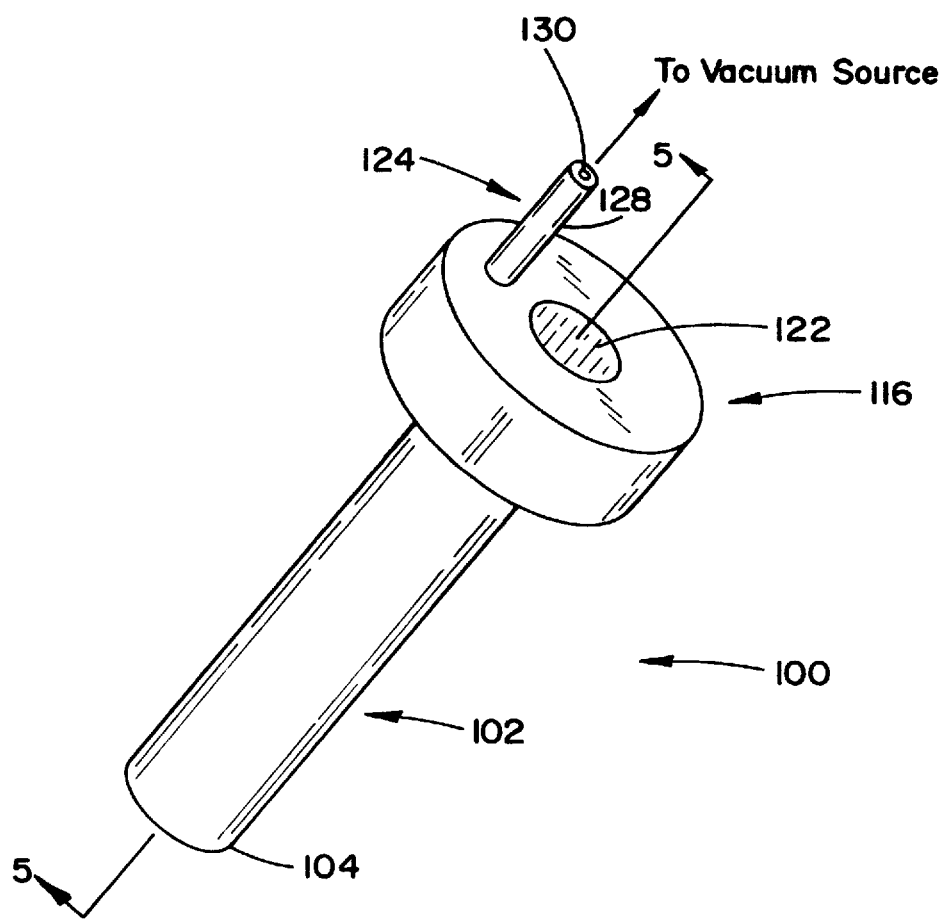
FIG. 4 illustrates an isometric view of the present invention.
Figure 5:
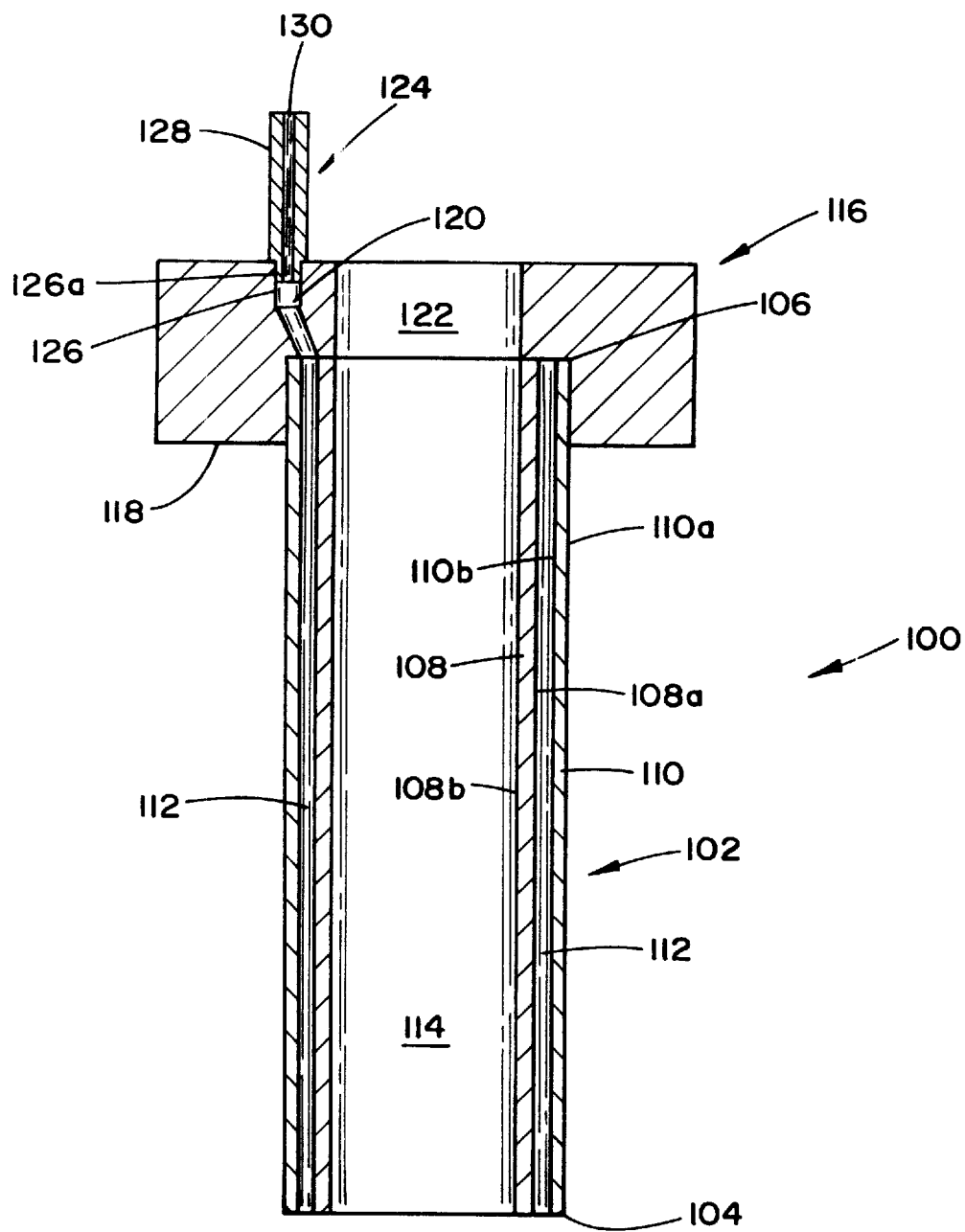
FIG. 5 illustrates a sectional view of the present invention taken along line 5—5 in FIG. 4.

Referring now in detail to FIGS. 3, 4, and 5, there is illustrated the inventive esophageal overtube 100 which includes a tube member 102. The tube member 102 has a distal end 104, a proximal end 106, an inner wall 108, and an outer wall 110. Each wall has an outside surface 108a, 110a and an inside surface 108b, 110b. The tube member further having a conduit 112 defined by the volume between the outside surface 108a of the inner wall 108 and the inside surface 110b of the outer wall 110. The conduit 112 extends from the distal end 104 to the proximal end 106 of the tube member 102. The tube member further having a lumen 114, defined by the inside surface 108b of the inner wall 108.

The tube member can be fabricated of any suitable medical grade material, preferably a polymer with good flexibility characteristics, such as silicone, nylon, PVC, or PTFE. The tube member is preferably fabricated from a unitary single piece multi-lumen tube as discussed later.

Figure 7A:
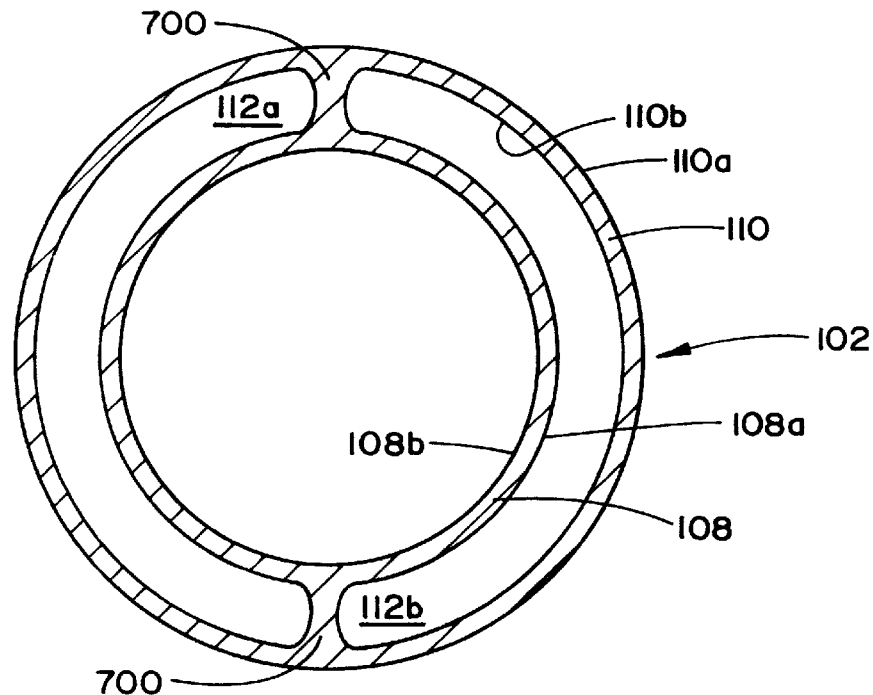
FIGS. 7A and 7B illustrate various sectional view configurations of the present invention as taken along line 7—7 in FIG. 6.
Figure 7B:
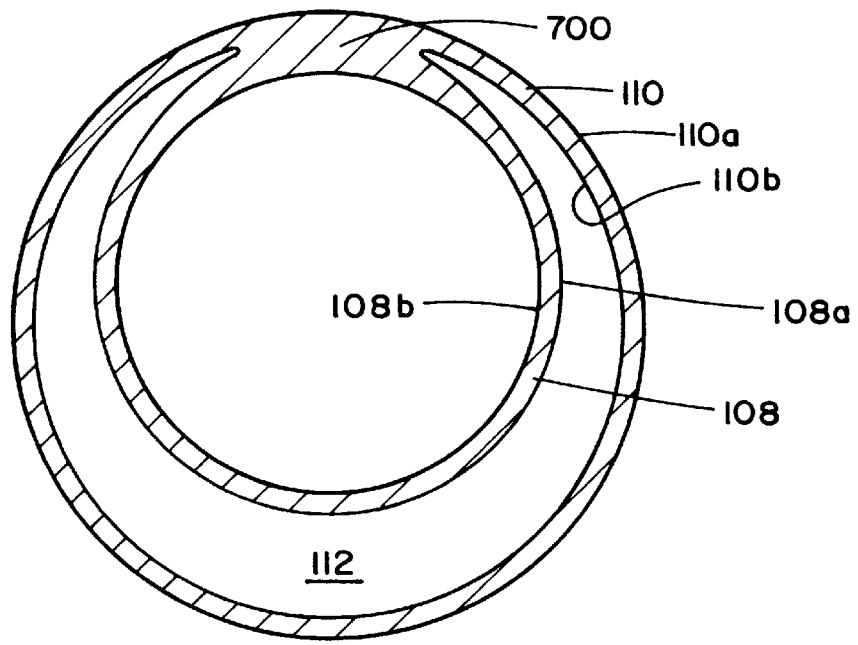

As shown in FIGS. 7A and 7B the cross-sectional shape of the inner and outer walls 108,110 of the tube member are preferably circular. However, any shape that can be accommodated by the esophagus, and which can accommodate an endoscope can be employed.

Typically, endoscopes of the type to be used for esophageal tumor ablation have an insertion tube with a cross-sectional diameter of 7.9 to 12.6 millimeters. By way of example only, and not as a limitation on the invention, it has been found that the outside diameter of the tube member 102 would need to be approximately 11.9 to 16.6 millimeters, respectively, to accommodate such endoscopes. The length of the tube member 102 would vary depending upon different size anatomies as well as for different locations of the tumor along the esophagus. Thus, several standard lengths would be fabricated, each to accommodate a range of tumor positions and anatomy sizes.

Referring back to FIGS. 3–5, a block 116 is disposed on the proximal end 106 of the tube member 102. The block having a counterbore 118 of substantially the same size and cross-sectional shape as the tube member 102 for acceptance of the proximal end 106 of the tube member 102. The tube member 102 is secured to the block 116 by any means known in the art, preferably with a suitable medical grade epoxy.

The block further having a conduit 120 in direct communication with the conduit 112 of the tube member 102, and an aperture 122 in direct communication with the lumen 114 of the tube member 102. The block can be fabricated from any suitable medical grade material, preferably a thermoplastic.

A vacuum port 124 is disposed on the block 116. The vacuum port has a conduit 130 in direct communication with the conduits 112, 120 of the tube member 102 and block 116. The vacuum port 124 further having an inlet end 126. The inlet end 126 of the vacuum port 124 having a stepped portion 126a of substantially the same size and cross-sectional shape as the conduit 120 of the block 116 for acceptance of the inlet end 126 into the conduit 120.

The vacuum port can be fabricated of any suitable medical grade material, preferably stainless steel. Securing the vacuum port 124 to the block 116 is accomplished by any means known in the art, preferably with a suitable medical grade epoxy.

The vacuum port 124 further has an outlet end 128 for connection to a vacuum source 300. The outlet end 128 being connected to the vacuum source 300 via medical grade tubing 302. The outlet end 128 can have any one of a number of different end configurations known in the art to facilitate connection of the tubing 302 to the outlet end 128. One such configuration is a tubular end, shown in FIGS. 4 and 5, commonly referred to in the art as a tube stub.

Figure 8A:
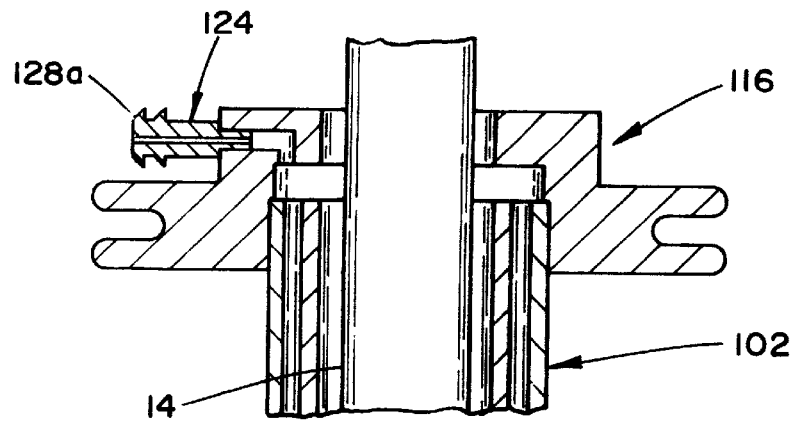
FIGS. 8A, 8B, and 8C illustrate partial sectional views of the various connector port configurations of the present invention.
Figure 8B:
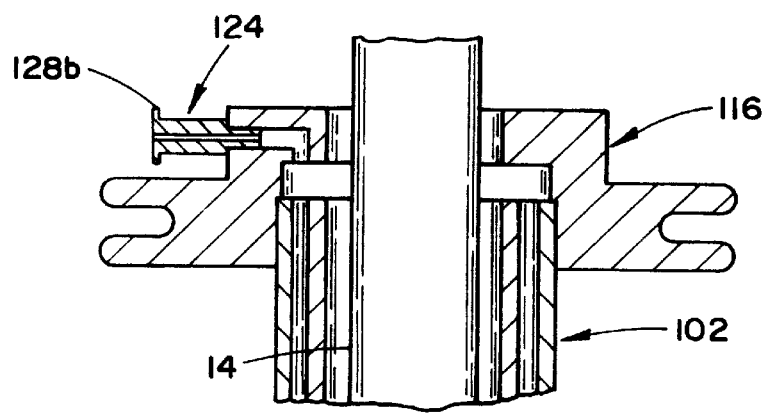
Figure 8C:
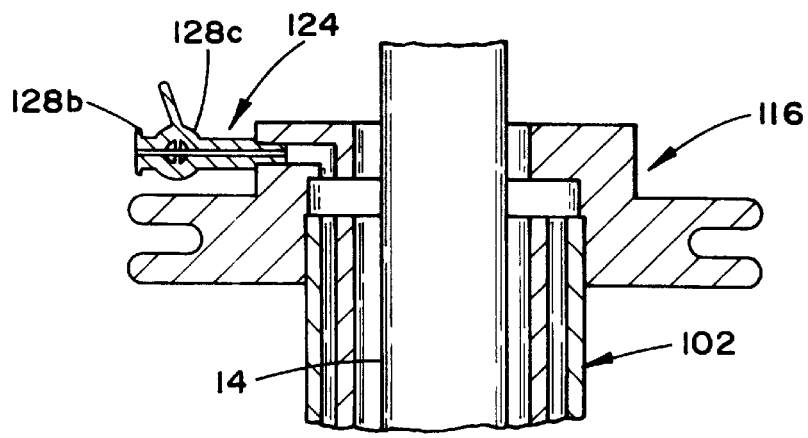

Referring now to FIGS. 8A, 8B, and 8C, the outlet end 128 can also be a barbed end 128a, a luer end 128b, or a stopcock 128c having a luer end 128b for facilitating the connection of the tubing 302.

Figure 6:
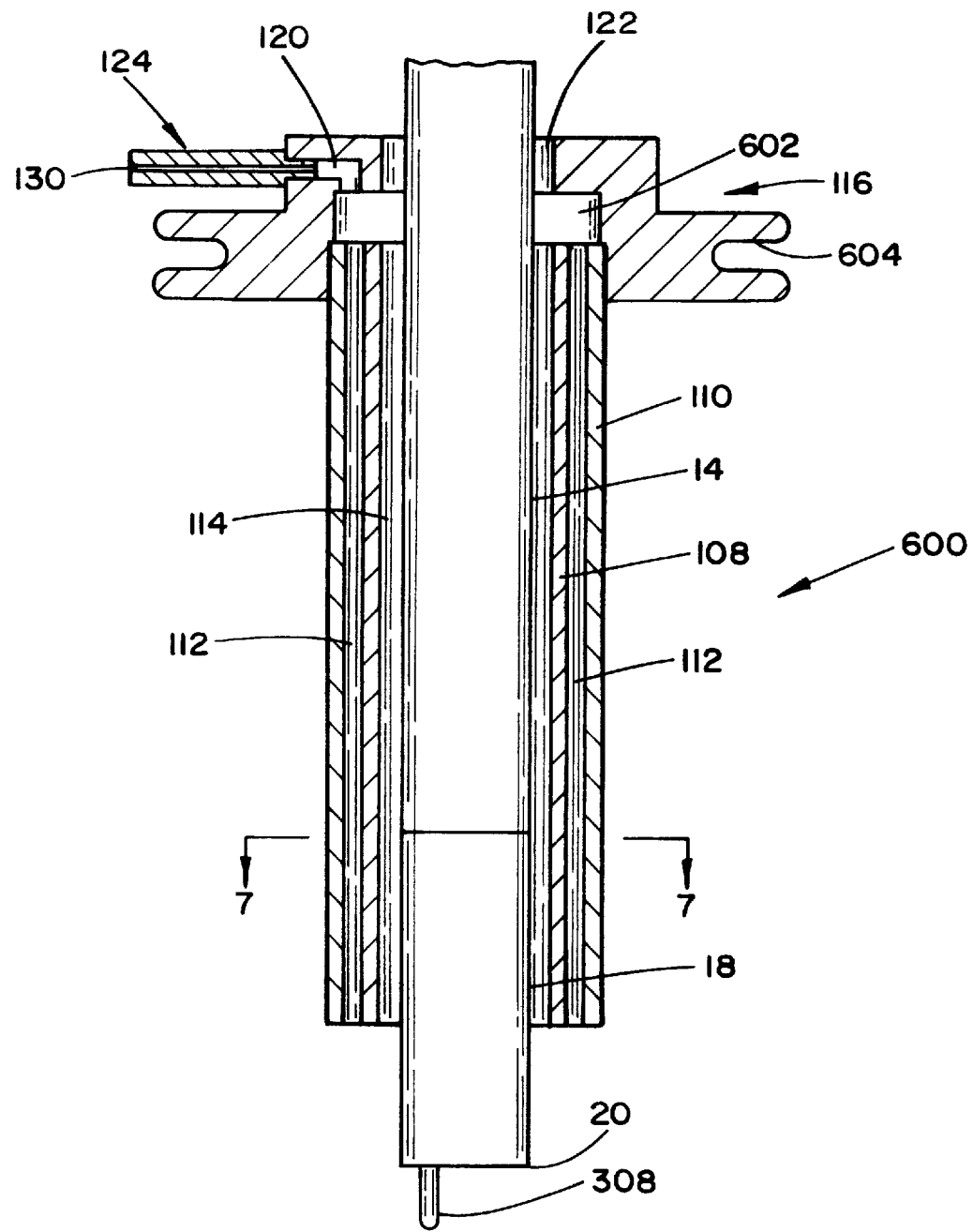
FIG. 6 illustrates a version of the present invention as it would be viewed along line 5—5 in FIG. 4.

Referring now to FIGS. 6, 7A, and 7B, in another version of the preferred embodiment, the tube member preferably has at least one web 700 connecting the inner and outer walls and maintaining a uniform spacing between them. The number and configuration of the webs can be any one of an endless number of varieties.

The web configuration is preferably in one of two variations. In a first variation, as shown in FIG. 7B, the inner wall 108 and outer wall 110 are circular in cross-section and non-concentric, whereby the outside surface 108a of the inner wall 108 and the inside surface 110b of the outer wall 110 intersect to form a web 700.

In a second variation, shown in FIG. 7A, two webs 700 are employed, equally spaced around the circular circumference of the inner and outer walls 108, 110. The webs 700, the inside surface 110b of the outer wall 110, and the outside surface 108a of the inner wall 108 define two conduits 112a, 112b of equal volume.

As shown in the embodiment illustrated in FIGS. 6 and 7A, referred to generally by reference numeral 600, a web 700 arrangement is used whereby more than one conduit 112a, 112b is created. To efficiently evacuate smoke from the distal end 104 of the overtube 600, there must be a means to communicate the conduits 112a, 112b with each other. The preferred method of achieving this communication is to provide a mixing chamber 602 in the block 116. The mixing chamber 602 is an annular bore positioned between the proximal end 106 of the tube member 102 and the conduit 120 of the block 116. The mixing chamber 602 allows the conduits 112a, 112b to both communicate with each other, and with the conduit 120 of the block 116. Therefore, the conduit 130 of the vacuum port 124 is in communication with both conduits 112a, 112b of the tube member 102.

However, it should be understood that any means for achieving this communication can be employed without departing from the scope and spirit of the present invention. Another such means would be to provide holes (not shown)

in the webs 700 which would communicate from one conduit 112a to the other conduit 112b.

In another version of the preferred embodiment, as shown in FIG. 6, referred to generally by reference numeral 600, the block 116 further has portions defining a bite block 604. The size and shape of the portions defining the bite block 604 being of substantially the same size and shape as bite blocks currently employed in the art.

Figure 9:
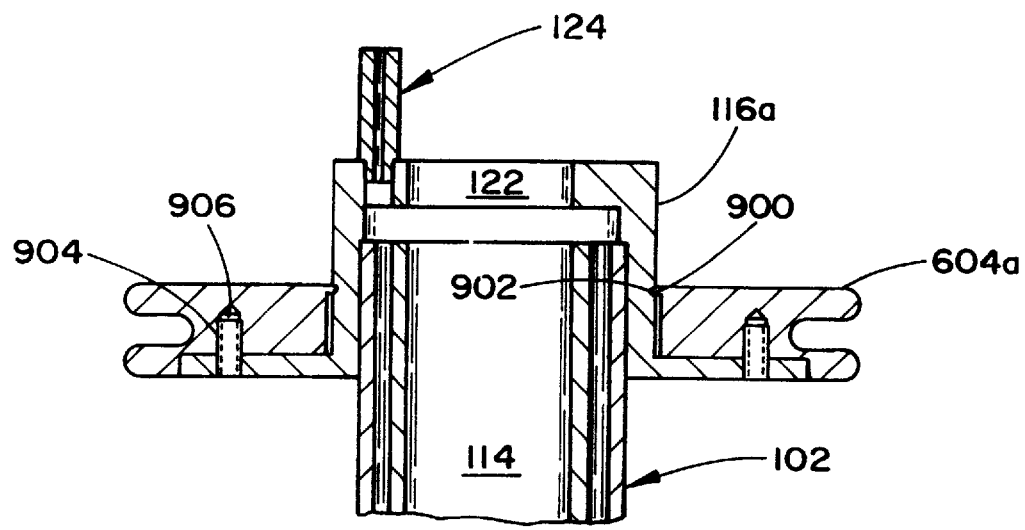
FIG. 9 illustrates a partial sectional view of the present invention configured with a two piece block.

In a variation of this embodiment, as shown in FIG. 9, the block 116a, and bite block 604a define two separate pieces. A means for securing the bite block 604a to the block 116a and a means for releasing the bite block 604a from the block 116a are provided in which a projection 900 is disposed on the bite block 604a, and an opposing indent 902 is disposed on the block 116a. The indent 902 is of substantially the same size and shape as the projection 900 of the bite block 604a such that an interference fit is produced between the projection 900 and the indent 902 when the bite block 604a is mated with the block 116a, but which can be easily pulled apart when necessary.

Further provided in the embodiment as shown in FIG. 9 is a means for locating the bite block 604a onto the block 116a in which at least one pin 904 is disposed on the block 116a. The bite block 604a further has at least one bore 906 opposing the pin 904 and being of substantially the same shape and size as the pin 904 for acceptance of the pin 904. Preferably, two pins are employed, 180° apart.

The block 116a is preferably constructed from a durable, resilient polymer which is capable of withstanding repeated cleaning, disinfecting, and/or sterilization, such as polysulfone. The bite block 604a is also preferably constructed of a polymer. The pins 904 being of a resilient material, preferably stainless steel, and force fit in place. In the embodiment described wherein the bite block 604a is removable from the block 116a, the bite block 604a can be made disposable whereby it is removed and disposed after each use.

Figure 10:
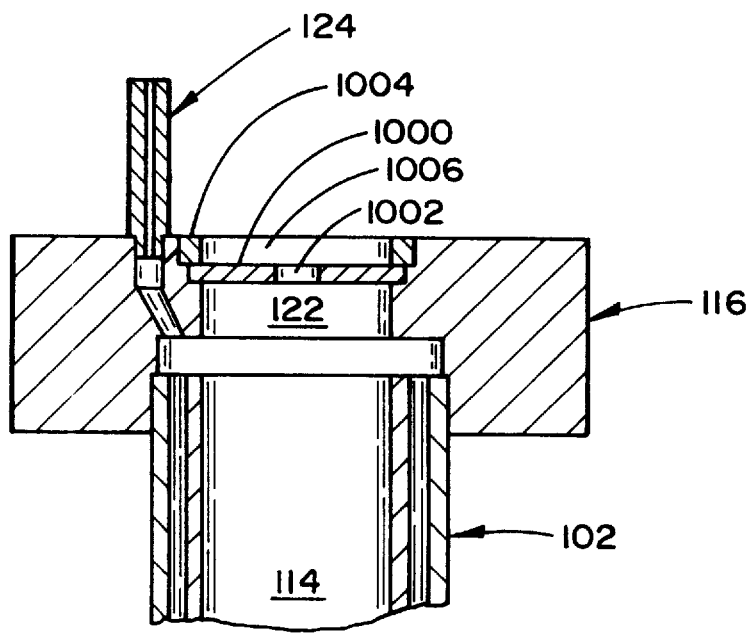
FIG. 10 illustrates a partial sectional view of the present invention configured with an elastomer membrane.

In yet another version of the preferred embodiment, as shown in FIG. 10, the block 116 further has a sealing means provided by an elastomer membrane 1000. The elastomer membrane has an aperture 1002 of smaller cross-sectional shape than the cross-sectional shape of the endoscope 10 to be inserted therein, whereby the membrane 1000 stretches to conform to the cross-sectional shape of the endoscope 10 when inserted into the aperture 1002 of the membrane 1000, thereby isolating the operating environment from the lumen 114 of the tube member 102.

The membrane 1000 can be fixed to the block 116 by any method known in the art, preferably by sandwiching it between the block 116 and a plate 1004. The plate 1004 being held in place by any suitable medical grade epoxy, or screws (not shown) of a suitable material, such as stainless steel. The plate 1004 further having an aperture 1006 of substantially the same size and shape as the aperture 122 of the block 116 for acceptance of the endoscope 10.

Figures 1, 2:
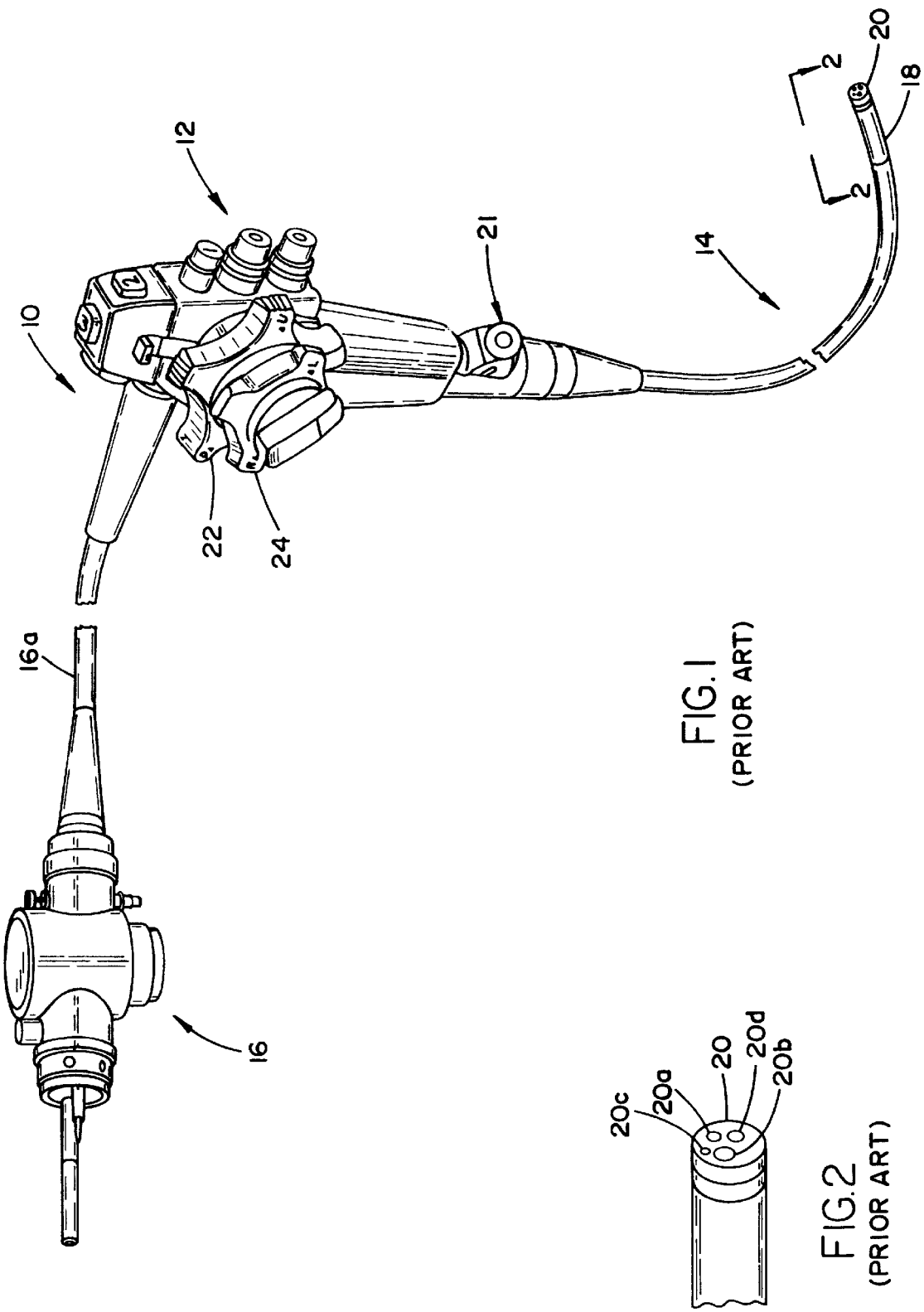
FIG. 1 illustrates an endoscope of the prior art.
FIG. 2 illustrates an enlarged view of the distal end of the endoscope of FIG. 1 as viewed along line 2—2.

Referring now to FIGS. 1, 2, and 3, the use of the esophageal overtubes of the present invention will be described in which the overtube 100 (or 600) is first inserted into the esophagus. If the overtube 600 is one which incorporates a bite block 604 or 604a, the patient bites down onto the bite block 604 or 604a. If the overtube 100, does not incorporate a bite block 604 or 604a, then one is inserted into the patients mouth and the patient bites down onto it.

The insertion tube 14 of an endoscope 10 is then inserted through the aperture 122 of the block 116, the lumen 114 of the tube member 102, and alternatively, the apertures 1002, 1006 of the elastomer membrane 1000 and plate 1004, respectively. The endoscope 10 is then advanced through the overtube 100 (or 600) until the distal end 20 is near the site of an esophageal tumor 304. A laser probe 306 is advanced through the working channel of the endoscope via the working channel inlet 21 until the laser probe tip 308 exits the working channel exit 20d. The laser probe tip 308 is directed at the tumor 304 by deflecting the bending section 18 by way of the up/down and right/left angulation knobs 22,24, located on the control head 12.

The laser probe 306 is connected to a laser generator 310 which energizes the laser probe 306 upon demand by the doctor. A light source 312 is used to illuminate the tumor 304 via the light guide 20a. The doctor preferably views the procedure on a video monitor 314. Video signals are supplied to the monitor 314 by a video processor 316 which receives and interprets the video signals from a CCD camera at the objective lens 20b. A documentation device, such as a VCR 318 can also be employed to produce a permanent record of the procedure.

When the laser is fired at the tumor 304, smoke is produced. Simultaneously, a vacuum is produced by the vacuum source 300 and applied via the tubing 302 and conduits 130, 112 of the vacuum port 124 and tube member 102 at the distal end 104 of the tube member 102. The vacuum source 300 evacuates the smoke from the distal end 104 to a remote site 320, so as not to expose operating room personnel to the carcinogens in the smoke.

Figure 11:
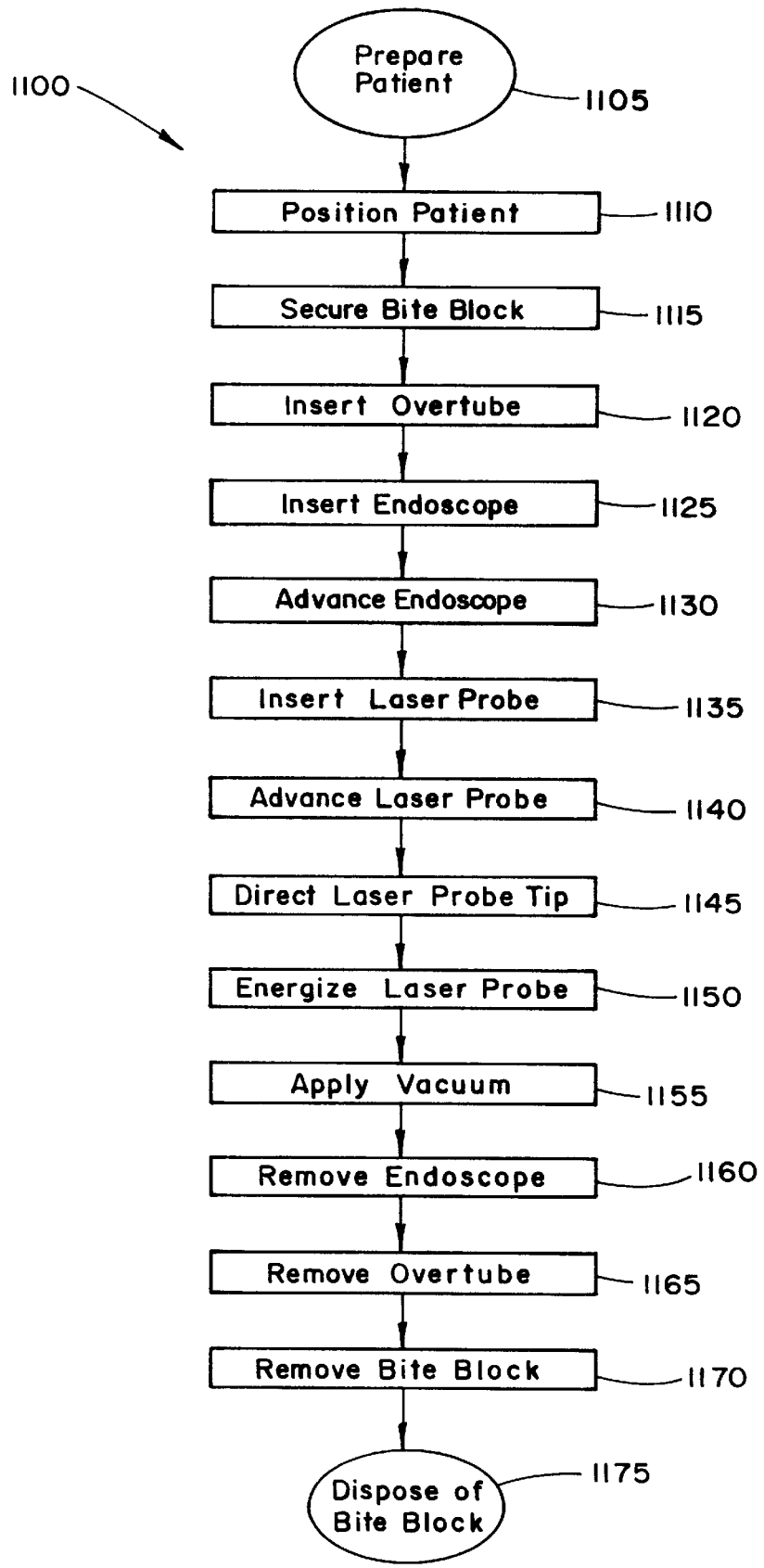
FIG. 11 illustrates a flow chart outlining the steps of a method for using the present invention.

Referring now to FIG. 11, methods for using the esophageal overtube of the present invention are discussed in connection with performing endoscopic tumor ablation with laser therapy.

Referring to FIG. 11, a flow chart is illustrated outlining the steps of an esophageal tumor ablation performed using endoscopic laser therapy and the embodiment of the present invention as shown in FIGS. 3 and 9 in which the bite block 604a is disposable. The procedure being generally referred to by reference numeral 1100.

The patient is first prepared at step 1105 for the endoscopic procedure. Preparation includes administering medication, spraying the patients throat with a topical anesthetic and removing dentures and any other oral foreign bodies from the oral cavity. The patient is then positioned on his side at step 1110, preferably with the left side down allowing any gastric secretions to pool away from the distal stomach.

The bite block 604a is secured at step 1115 to the block 116a by aligning the pins 904 with the bores 904 and sliding the bite block 604a over the block 116a until the projection 900 locks into the indent 902. If the esophageal overtube of the present invention as shown in FIGS. 4 and 5 is used, the step of securing 1115 the bite block 604a would be replaced by a step which inserts a bite block into the patients mouth. Similarly, if the esophageal overtube of the present invention as shown in FIG. 6 is used, the step of securing 1115 the bite block 604a would be eliminated since in that embodiment, the bite block 604 is integral with the block 116.

Referring back to FIG. 11, the tube member 102 of the esophageal overtube is inserted in place in the patient's esophagus at step 1120 whereby the bite block 604a resides in the patient's oral cavity for the patient to bite down upon. The endoscope 10 is then inserted at step 1125 through the aperture 122 of the bite block 604a and the lumen 114 of the tube member 114. If the embodiment of the present invention includes a sealing membrane 1000, as is shown in FIG. 10, then the step of inserting 1125 the endoscope also isolates the lumen 114 from the operating environment thus providing for a more efficient evacuation of laser smoke.

The endoscope 10 is then advanced at step 1130 until its distal end 20 reaches the site of the esophageal tumor 304. The doctor can see the tumor 304 and determine the tumors distance from the distal end 20 by observing a live image of the esophagus interior on the video monitor 314.

A laser probe 306 is then inserted at step 1135 into the working channel inlet 21 of the endoscope 10 and advanced 1140 through the working channel until the laser probe tip 308 emerges from the working channel outlet 20d on the distal end 20. The laser probe tip 308 is directed at the tumor 304 at step 1145 by angulating the bending section 18 by way of the up/down and right/left angulation knobs 22,24 on the endoscopes control head 12.

The laser probe 306 is then energized at step 1150 upon demand by the doctor with the help of the laser generator 310. The laser probe tip then emits a laser which ablates the tumor creating smoke and burnt tissue. The steps of directing 1145 the laser probe tip 308 at the tumor 304 and energizing 1150 the laser probe 304 are repeated until a satisfactory amount of tumor is ablated.

Simultaneous with the energizing step 1150 of the laser probe 304 a vacuum is applied at step 1155 to the vacuum port 124 of the esophageal overtube for evacuating the laser smoke and burnt tissue created by the laser probe 304. The smoke and burnt tissue are evacuated through the conduit 112 of the tube member, into the mixing chamber 602, through the conduit 120 of the block, through the conduit 130 of the vacuum port 124, and through the vacuum tubing 16a to a remote site 320.

After satisfactory ablation is completed, the endoscope is removed at step 1160, the overtube is removed at step 1165 from the patient's esophagus, the bite block 604a is removed at step 1170 from the overtube, and lastly the bite block 604a is disposed at step 1175. Again, the disposal 1175 of the bite block 604a is eliminated if an embodiment other than that shown in FIG. 9 is used.

From the foregoing, it becomes readily apparent to one skilled in the art that the novel esophageal overtube of the present invention offers increased safety and efficiency over currently employed devices. Due to the inventive overtube arrangement, wherein two walls are used to construct the tube member, the advantages offered by the inventive structure resides in:

(a) operating room personnel are not exposed to cancerous aerosols which may be contained in laser smoke produced in endoscopic tumor ablation in the esophagus;

(b) the evacuation of smoke at the point where it is being produced serves to keep the endoscope's lens cleaner, for a longer period, reducing the number of times the endoscope needs to be removed from the patient for cleaning;

(c) reducing the number of times the endoscope needs to be removed during a procedure reduces doctor inconvenience, procedure length, and the amount of patient discomfort and trauma;

(d) reducing the cost of the procedure because the need for a two-channeled endoscope is eliminated, thereby allowing the more economical single-channeled endoscope to be used;

(e) reducing the amount of dexterity required by a doctor using a two-channeled endoscope;

(f) providing a more efficient evacuation of laser smoke than what is provided by evacuation through a relatively small working channel; and (g) reducing the cost of the procedure because the need for an expensive exhaust hood is eliminated;

(h) further reduces the amount of patient discomfort and trauma associated with the larger two-channeled endoscopes.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

I claim:

1. An esophageal overtube for use with an endoscope, the esophageal overtube comprising:

a unitary single piece tube member having a distal end, a proximal end, an inner wall, an outer wall, each wall having an outside and inside surface, a conduit defined by the volume between the outside surface of the inner wall and the inside surface of the outer wall, the conduit extending from the distal end to the proximal end, the tube member further having a lumen defined by the inside surface of the inner wall, the inner and outer walls being connected by at least one web portion;

a block disposed on the proximal end of the tube member, the block having a conduit in direct communication with the conduit of the tube member, and an aperture in direct communication with the lumen of the tube member for passage of the endoscope therethrough; and a vacuum port disposed on the block, the vacuum port having a conduit in direct communication with the conduits of the block and tube member, and an outlet end for connection to a vacuum source, for evacuating smoke from the distal end of the tube member through the conduits of the block, tube member, and vacuum port.

2. The esophageal overtube as claimed in claim 1, wherein the walls of the tube member are circular in cross section.

3. The esophageal overtube as claimed in claim 2, wherein the inner and outer walls are non-concentric, whereby a point of intersection between the outer surface of the inner wall and the inner surface of the outer wall forms the web connecting the inner and outer walls.

4. The esophageal overtube as claimed in claim 1, wherein the at least one web connecting the inner and outer walls of the tube member, the volume between the outside surface of the inner wall, the inside surface of the outer wall and adjacent webs each defining a conduit, the number of conduits being equal to the number of webs, the esophageal overtube further comprising a mixing chamber disposed in the block having surfaces defining a volume common to the conduits of the tube member, wherein the conduit of the block is in direct communication with the mixing chamber.

5. The esophageal overtube as claimed in claim 4, wherein there are two webs defining two conduits of substantially equal volume.

6. The esophageal overtube as claimed in claim 1, wherein the block further having portions defining a bite block for a patient to bite upon when the esophageal overtube is in place in the patient's esophagus.

7. The esophageal overtube as claimed in claim 6, wherein the block and the bite block portions define two separate pieces, and further comprising means for securing the bite block to the block and means for releasing the bite block from the block.

8. The esophageal overtube as claimed in claim 7, wherein the means for securing the bite block to the block and the means for releasing the bite block from the block comprises a projection disposed on the bite block, and an opposing indent disposed on the block, the indent being of substantially the same size and shape as the projection such that an interference fit is produced when the bite block is mated with the block but which can be easily pulled apart to overcome the interference fit.

9. The esophageal overtube as claimed in claim 7, further comprising means for locating the bite block onto the block.

10. The esophageal overtube as claimed in claim 9, wherein the means for locating the bite block onto the block comprises a pin disposed on the block, the bite block further having a bore opposing the pin, the bore being substantially the same size and shape as the pin for acceptance of the pin.

11. The esophageal overtube as claimed in claim 7 wherein the bite block is disposable.

12. The esophageal overtube as claimed in claim 1 wherein the tube member material is one of silicone, nylon, PVC, or PTFE.

13. The esophageal overtube as claimed in claim 1 further comprising one of a barbed fitting, luer fitting, and stopcock fitting disposed on the outlet end of the vacuum port.

14. The esophageal overtube as claimed in claim 1 further comprising sealing means disposed in the aperture of the block for isolating the lumen of the tube member from the operating environment.

15. The esophageal overtube as claimed in claim 14 wherein the sealing means comprises:

an elastomer membrane having an aperture of smaller cross-sectional shape than the cross-sectional shape of the endoscope to be inserted therein, whereby the membrane stretches to conform to the cross-sectional shape of the endoscope when inserted into the aperture of the membrane thereby isolating the operating environment from the lumen of the tube member; and securing means for securing the elastomer membrane to the block.

16. The esophageal overtube as claimed in claim 15 wherein the securing means comprises a plate fixed to the block such that the elastomer membrane is sandwiched between the plate and the block, the plate having an aperture in direct communication with the aperture of the elastomer membrane for acceptance of the endoscope therein.

17. A method for performing an endoscopic esophageal tumor ablation procedure using an endoscope and an esophageal overtube, the endoscope having an insertion tube having a distal end and a bending section, a working channel disposed in the insertion tube and having an inlet and an outlet at the distal end, and an angulation means for angulating the bending section, the method comprising the steps of:

providing an esophageal overtube, for use with the endoscope, the esophageal overtube comprising a unitary single piece tube member having a distal end, a proximal end, an inner wall, an outer wall, each wall having an outside and inside surface, a conduit defined by the volume between the outside surface of the inner wall and the inside surface of the outer wall, the conduit extending from the distal end to the proximal end, the tube member further having a lumen defined by the inside surface of the inner wall, the inner and outer walls being connected by at least one web portion; a block disposed on the proximal end of the tube member, the block having a conduit in direct communication with the conduit of the tube member, and an aperture in direct communication with the lumen of the tube member for passage of the endoscope therethrough; and a vacuum port disposed on the block, the vacuum port having a conduit in direct communication with the conduits of the block and tube member, and an outlet end for connection to a vacuum source;

preparing the patient by administering medication and/or topical anesthetic;

positioning the patient in a manner which facilitates effective performance of the procedure;

inserting the esophageal overtube into the patients esophagus;

inserting the insertion tube of the endoscope into the esophageal overtube;

advancing the insertion tube until the distal end of the endoscope reaches the site of the tumor;

inserting a laser probe having a tip and connected to a laser generator into the working channel;

advancing the laser probe until the laser probe tip emerges from the working channel outlet;

directing the laser probe tip at the tumor by angulating the bending section via the angulation means;

energizing the laser probe via the laser generator for ablation of the tumor;

applying vacuum to the esophageal overtube such that laser smoke and burnt tissue generated by the energizing of the laser is evacuated from the distal end of the tube member through the conduits of the block, tube member, and vacuum port and into a remote site;

removing the endoscope from the esophageal overtube; and removing the overtube from the patient's esophagus.

18. The method as claimed in claim 17 further comprising the steps of:

securing a disposable bite block to the esophageal overtube before insertion of the endoscope into the esophageal overtube;

removing the disposable bite block from the esophageal overtube after removal of the overtube from the patient's esophagus; and disposing of the bite block.

19. The method as claimed in claim 17 wherein the step of inserting the endoscope further comprises a simultaneous sealing of the esophagus from the operating environment.

* * * * *